(12) United States Patent
Sumida et al.

(10) Patent No.: US 6,776,983 B1
(45) Date of Patent: Aug. 17, 2004

(54) PROTEIN FREE FORMULATIONS

(75) Inventors: Shuji Sumida, Tokyo (JP); Yasushi Sato, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/622,487

(22) PCT Filed: Mar. 5, 1999

(86) PCT No.: PCT/JP99/01080

§ 371 (c)(1),
(2), (4) Date: Aug. 17, 2000

(87) PCT Pub. No.: WO99/44630

PCT Pub. Date: Sep. 10, 1999

(30) Foreign Application Priority Data

Mar. 6, 1998 (JP) .......................................... 10/054799

(51) Int. Cl.[7] .............................................. A61K 38/17
(52) U.S. Cl. ............................ 424/85.1; 514/8; 514/21
(58) Field of Search ............................... 514/8, 12, 21; 530/351, 399; 424/85.1

(56) References Cited

U.S. PATENT DOCUMENTS 5,202,117 A * 4/1993 Tsuji et al. ................. 424/85.1
5,503,827 A * 4/1996 Woog ......................... 424/85.1
5,919,443 A * 7/1999 Michaelis ................... 424/85.1
5,919,757 A * 7/1999 Michaelis ....................... 514/8

FOREIGN PATENT DOCUMENTS

| JP | 63-146826 | | 6/1988 |
| JP | 4-77436 | * | 3/1992 |
| JP | 5-339164 | * | 12/1993 |
| JP | 6-510031 | | 11/1994 |
| JP | 8-504784 | | 5/1996 |
| JP | 8-505610 | | 6/1996 |

OTHER PUBLICATIONS

Copy of the International Search Report mailed Jun. 8, 1999 from the Japanese Patent Office.

Oh–oda, M. et al., J. Biol. Chem., 265(20), 11432–11435, 1990.

\* cited by examiner

Primary Examiner—Jeffrey Edwin Russel
(74) Attorney, Agent, or Firm—Morgan & Finnegan, LLP

(57) ABSTRACT

A stable granulocyte colony-stimulating factor-containing formulation comprising a granulocyte colony-stimulating factor and at least one pharmaceutically acceptable surfactant in an amount of 1 part by weight or less per part by weight of the granulocyte colony-stimulating factor and having a pH of 7 or less.

9 Claims, 3 Drawing Sheets

Percentage (%) of remaining G-CSF after acceleration at 40 °C for 2 weeks

Content (%) of desialylated G-CSF after acceleration at 40 °C for 2 weeks

PROTEIN FREE FORMULATIONS

FIELD OF THE INVENTION

The present invention relates to granulocyte colony-stimulating factor-containing formulations, and particularly granulocyte colony-stimulating factor-containing formulations stabilized by preventing loss and inactivation of active Ingredients due to adsorption to container walls, aggregation, polymerization, oxidation or the like.

PRIOR ART

Granulocyte colony-stimulating factor (hereinafter also referred to as "G-CSF") is a glycoprotein having a molecular weight of about 20,000 and acting on precursor cells of neurophils to promote their proliferation and differentiation to maturation.

Since we purified high-purity human G-CSF by culturing a cell line collected from tumor cells of a patient with cancer of the floor of the mouth, the human G-CSF gene was successfully cloned and, at present, recombinant human G-CSF can be produced in mass in animal cells by genetic engineering. We also succeeded in converting this purified G-CSF into a formulated product, which Is supplied to the market as an antiinfective agent (Japanese Patent No. 2116515).

G-CSF is used in a very small amount, i.e. a formulation containing 0.1–1000 µg (preferably 5–500 µg) of G-CSF is normally administered once to seven times per week per adult. However, this G-CSF is adsorptive to walls of ampoules, syringes or the like. G-CSF is also unstable and susceptible to extrinsic factors such as temperature, humidity, oxygen, UV rays or the like to undergo physical or chemical changes including aggregation polymerization or oxidation, resulting in great loss of activity.

Thus, various formulation designs have been made to supply stable G-CSF formulations to the market. For example, formulations containing a buffer selected from acetic acid, lactic acid, citric acid, maleic acid, phosphoric acid and salts thereof or arginine and salts thereof were proposed (JPA No. 505610/96). G-CSF formulations containing 1–10,000 parts by weight of a surfactant as a stabilizer per part by weight of G-CSF were also proposed (JPA No. 146826/88). The latter publication describes that the level of the surfactant, particularly its lower limit is critical to prevent loss of G-CSF and to achieve stabilization in G-CSF-containing liquid formulations.

An object of the present invention is to provide a G-CSF formulation, which enables a reduction in the complexity of the production process and which is more stable for extended storage.

SUMMARY OF THE INVENTION

As a result of careful studies to achieve the above object, we accomplished the present invention on the basis of the finding that a stable G-CSF liquid formulation can be obtained even when it contains a very small amount of a surfactant as a stabilizer.

Accordingly, the present invention provides a stable granulocyte colony-stimulating factor-containing formulation comprising a granulocyte colony-stimulating factor and 0.0001–1 parts by weight of at least one pharmaceutically acceptable surfactant per part by weight of the granulocyte colony-stimulating factor and having a pH of 7 or less.

As used herein, stabilization means that the percentage of remaining G-CSF is kept at 95% or more after storage at 25° C. for 6 months or 75% or more after storage at 40° C. for 2 weeks.

THE MOST PREFERRED EMBODIMENTS OF THE INVENTION

Figure 1:
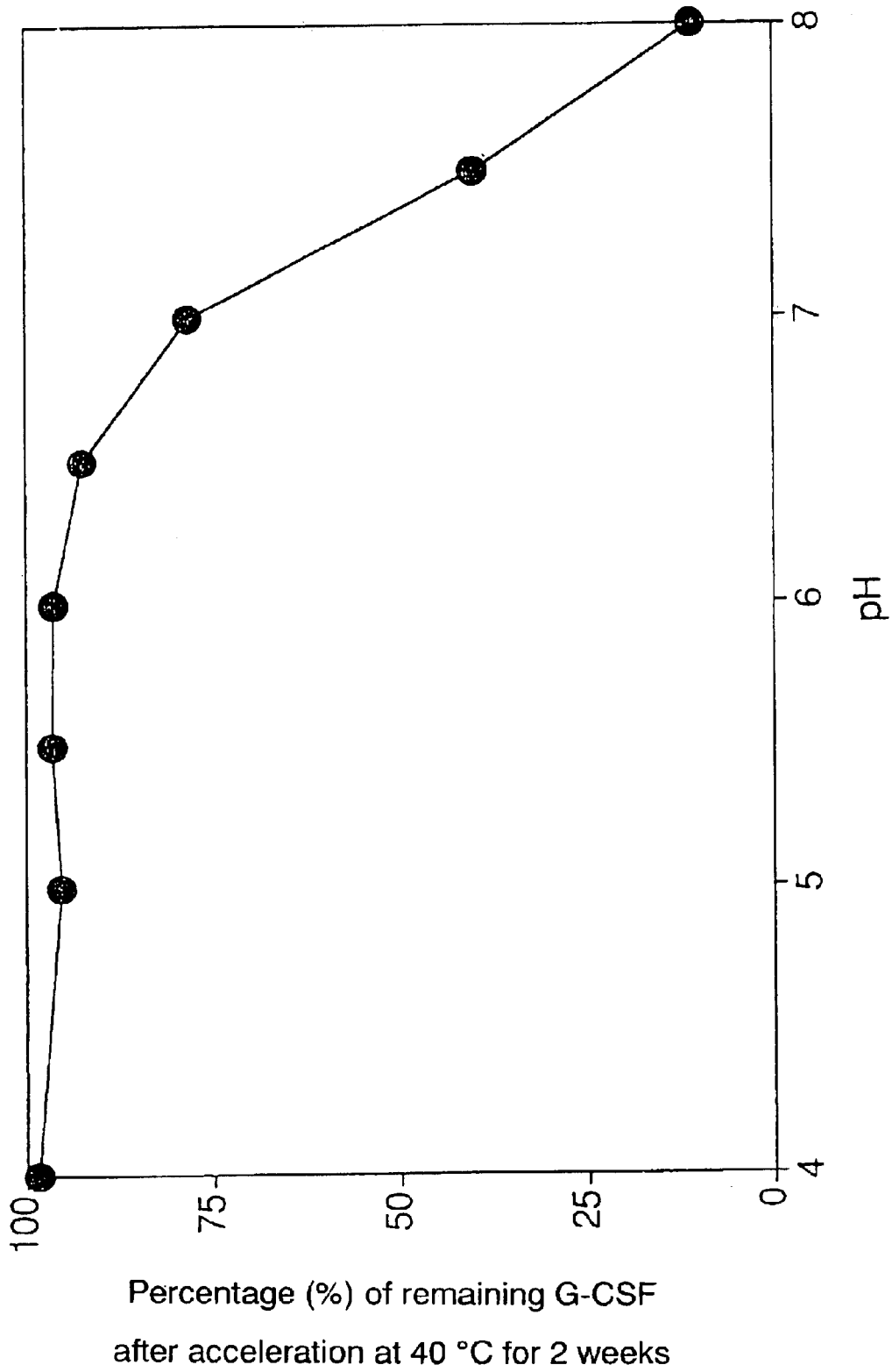
FIG. 1 is a graph showing the relationship between pH and the percentage of remaining G-CSF after an acceleration test at 40° C. for 2 weeks.

Any high-purity human G-CSF may be used for liquid formulations of the present invention. Specifically, it may be derived from natural sources or obtained by genetic recombination so far as it has substantially the same biological activity as that of mammalian, particularly human G-CSF. Genetically recombinant G-CSF may have the same amino acid sequence as that of natural G-CSF or may contain deletion, substitution or addition of one or a plurality of amino acids in said amino acid sequence so far as it has said biological activity. G-CSF in the present invention may be prepared by any process, e.g., they may be extracted and purified by various techniques from cultures of a human tumor cell line or may be produced by genetic engineering in cells of E. coli, yeast, Chinese hamster ovary (CHO), C127 or the like and then-extracted and purified by various techniques. Most preferably, G-CSF is produced in CHO cells by genetic recombination.

Typical examples of surfactants suitable for obtaining stable G-CSF-containing formulations of the present invention include nonionic surfactants, e.g., sorbitan fatty acid esters such as sorbitan monocaprylate, sorbitan monolaurate, sorbitan monopalmitate: glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate: polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polypxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having a HLB of 6–18; cationic surfactants, e.g., alkyl sulfates having a C10–18 alkyl group such as sodium cetylsulfate, sodium laurylsulfate, sodium oleylsulfate; polyoxyethylene alkyl ether sulfates having an average number of EO moles of 2–4 and a C10–18 alkyl group such as sodium polyoxyethylene laurylsulfate; alkyl sulfosuccinic acid ester salts having a C8–18 alkyl group such as sodium laurylsulfosuccinate; natural surfactants, e.g., lecithin; grycerophospholipids; sphingophospholipids such as sphingomyelin; sucrose fatty acid esters of fatty acids containing 12 to 18 carbon atoms.

One or two or more of these surfactants may be added to liquid formulations of the present invention.

Preferred surfactants are polyoxyethylene sorbitan fatty acid esters, more preferablly Polysorbates 20, 21, 40, 60, 65, 80, 81, 85, most preferably Polysorbates 20 and 80.

The amount of surfactants to be added to G-CSF-containing formulations of the present invention is typically 0.0001–1 parts by weight per part by weight of G-CSF, preferably 0.01–1 parts by weight per part by weight of G-CSF, more preferably 0.2–1 parts by weight per part by weight of G-CSF, even more preferably 0.2–0.8 parts by weight per part by weight of G-CSF, most preferably 0.4–0.8 parts by weight per part by weight of G-CSF. Particularly when 125 $\mu$g or 250 $\mu$g of G-CSF is contained per mL of formulations, 100 $\mu$g of surfactants are preferably added. Therefore, 0.4 parts by weight or 0.8 parts by weight of surfactants are especially preferred per part by weight of G-CSF. When any protein such as albumin is not added as a stabilizer, the percentage of remaining G-CSF tended to decrease after extended storage in the presence of surfactants exceeding 1 part by weight per part by weight of G-CSF. Even 1 part by weight or less of surfactants per part by weight of G-CSF can sufficiently inhibit adsorption of G-CSF to containers.

Preferred G-CSF-containing formulations of the present invention are substantially free from protein as a stabilizer. Some products on the market contain a protein such as human serum albumin or purified gelatin as a stabilizer for inhibiting chemical or physical changes of G-CSF. However, the addition of a protein as a stabilizer involves a very complicated process for removing contamination with viruses or other problems.

G-CSF-containing formulations of the present invention have a pH of 7 or less, preferably 5–7, more preferably 6–6.8, most preferably 6.2–6.8. As will be described later, the percentage of remaining G-CSF after an acceleration test at 40° C. for 2 weeks is stable at a pH of 7 or less. From this viewpoint, the pH is preferably about 7.0 or less. The production ratio of desialylated G-CSF determined after an acceleration test at 40° C. for 2 weeks showed a rapid increase of the content of desialylated products at pH 4 or less. From this viewpoint, the pH is preferably about 5 or more. Further taking into account the preference for neutrality which Is less irritable to human bodies for administration as injection formulations, the pH is most preferably 6.2–6.8.

G-CSF-containing formulations of the present invention may contain diluents, solubilizing agents, isotonizing agents, excipients, pH-modifiers, soothing agents, sulfur-containing reducing agents, antioxidants or the like. For example, isotonizing agents include polyethylene glycol; and sugars such as dextran, mannitol, sorbitol, inositol, glucose, fructose, lactose, xylose, mannose, maltose, sucrose, raffinose. Surfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as ethylenediamine tetraacetic acid disodium salt (EDTA), sodium pyrophosphate, sodium metaphosphate. As excipients may be added amino acids such as glycine, cysteine, threonine, cystine, tryptophan, methionine, lysine, hydroxylysine, hystidine, arginine. Other components commonly added to liquid formulations may also be contained, e.g. inorganic salts such as sodium chloride, potassium chloride, calcium chloride, sodium phosphate, potassium phosphate, sodium bicarbonate; and organic salts such as sodium citrate, potassium citrate, sodium acetate.

The amount of G-CSF contained in liquid formulations of the present invention depends on the nature of the disease to be treated, the severity of the disease, the age of the patient or other factors, but generally ranges from 1 to 1000 $\mu$g/mL, preferably 10 to 800 $\mu$g/mL, more preferably 50 to 500 $\mu$g/mL.

Liquid formulations of the present invention can be prepared by dissolving these components in an aqueous buffer known in the art of liquid formulations such as phosphate and/or citrate buffers. Preferred phosphate buffers are sodium monohydrogen phosphate—sodium dihydrogen phosphate series, and preferred citrate buffers are sodium citrate buffers.

Stabilized G-CSF-containing formulations of the present invention are normally administered via parenteral routes such as injection (subcutaneous, intravenous or intramuscular injection) or percutaneous, mucosal, nasal or pulmonary administration, but may also be orally administered.

G-CSF-containing formulations of the present invention are normally packed in a sealed and sterilized plastic or glass container. The container may be provided as a defined dosage form, such as an ampoule, vial or disposable syringe, or may be provided as a large dosage form such as a bag or bottle for injection. Preferably, G-CSF-containing formulations are provided as a dosage form packed in a vial, ampoule or prefilled syringe.

G-CSF-containing formulations of the present invention show a very good percentage of remaining G-CSF even after an acceleration test at 40° C. for 2 weeks or storage at 25° C. for 6 months as shown in the examples below. The sugar chain of G-CSF has one or two terminal sialic acids, which may be cleaved during extended storage. G-CSF-containing formulations of the present invention were found to keep a low production ratio of desialylated products even after an acceleration test at 40° C. for 2 weeks. Moreover, G-CSF-containing formulations of the present invention can sufficiently inhibit adsorption to containers and show a very good percentage of remaining G-CSF after an acceleration test at 40° C. for 2 weeks and after storage at 25° C. for 6 months irrespective of the shape of the container such as a vial or syringe.

The following examples further illustrate the present invention, without limiting the same thereto.

EXAMPLES

Experimental Procedure

A mixture of 250 mg of G-CSF, 0.1 g of Polysorbate 20 and 30 g of D-mannitol was weighed and adjusted to various pHs shown in the following Table 1 with a sodium phosphate buffer, and then brought to a total amount of 1 L.

TABLE 1

| pH | G-CSF | Poly-sorbate 20 | Man-nitol | Sodium phosphate buffer | Total amount |
|---|---|---|---|---|---|
| 4.0 | 250 mg | 0.1 g | 30 g | Equivalent to 25 mM | 1 L |
| 5.0 | 250 mg | 0.1 g | 30 g | Equivalent to 25 mM | 1 L |
| 5.5 | 250 mg | 0.1 g | 30 g | Equivalent to 25 mM | 1 L |
| 6.0 | 250 mg | 0.1 g | 30 g | Equivalent to 25 mM | 1 L |
| 6.5 | 250 g | 0.1 g | 30 g | Equivalent to 25 mM | 1 L |
| 7.0 | 250 mg | 0.1 g | 30 g | Equivalent to 25 mM | 1 L |
| 7.5 | 250 mg | 0.1 g | 30 g | Equivalent to 25 mM | 1 L |
| 8.0 | 250 mg | 0.1 g | 30 g | Equivalent to 25 mM | 1 L |

Each formulated solution was sterilely prepared and filtrated, after which 1 mL each was sterilely packed into a vial and sealed to prepare a G-CSF liquid formulation.

Thus sterilely prepared formulation containing 250 μg/mL of G-CSF was allowed to stand in an incubator at 40° C. for 2 weeks.

The content of G-CSF in each vial was determined according to the following method 1. The content of desialylated G-CSF in each vial was determined according to the following method 2.

Method 1

Pure water, acetonitrile and trifluoroacetic acid were used as mobile phase on a C4 reverse phase column (4.6 mm×250 mm, 300 angstroms). The content of G-CSF was determined by reverse phase high-performance liquid chromatography. The amount equivalent to 5 μg of G-CSF was injected and G-CSF was eluted with an acetonitrile gradient and spectroscopically detected at a wavelength of 215 nm.

The G-CSF content determined by this method was used to calculate the remaining percentage (%) after acceleration at 40° C. for 2 weeks according to the following equation.

Remaining percentage (%)=[(G-CSF content after acceleration at 40° C. for 2 weeks)/(G-CSF content without acceleration)]×100

Method 2

Desialylated G-CSF (with all the sialic acids of the sugar chain cleaved) and G-CSF (intact) were detected by cation exchange high-performance liquid chromatography. Namely, both were eluted with an NaCl gradient (0–500 mM) on a cation exchange column (TSK gel DEAE) using 20 mM Tris-HCL buffer (pH 7.4) as mobile phase and spectroscopically detected at a wavelength of 215 nm.

The values of desialylated G-CSF and intact G-CSF determined by this method were used to calculate the production ratio (%) of desialylated G-CSF after acceleration at 40° C. for 2 weeks according to the following equation.

Production ratio of desialylated G-CSF (%)={(desialylated G-CSF)/[(desialylated G-CSF)+(intact G-CSF)]}×100

Example 1

Effect of Varying pHs on the Percentage of Remaining G-CSF

The percentage of remaining G-CSF was calculated according to the equation of Method 1 after the liquid formulations prepared at varying pHs shown in Table 1 were subjected to an acceleration test at 40° C. for 2 weeks. The results are shown in FIG. 1.

At a pH of 7 or less, the percentage of remaining G-CSF was 75% or more.

Example 2

Effect of Varying pHs on the Production of Desialylated G-CSF

Figure 2:
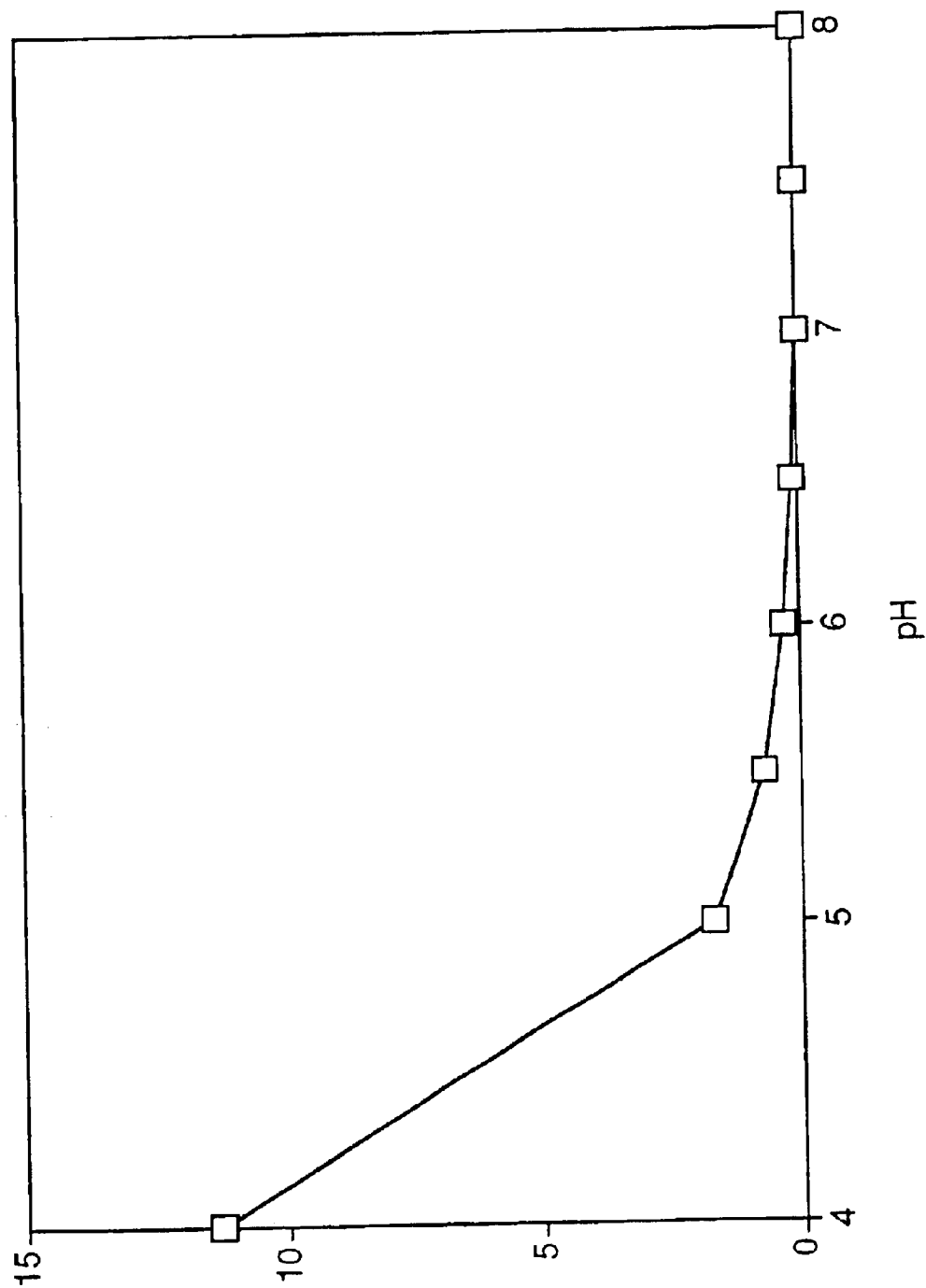
FIG. 2 is a graph showing the relationship between pH and the production ratio of desialylated G-CSF after an acceleration test at 40° C. for 2 weeks.

The production ratio of desialylated G-CSF was calculated according to the equation of Method 2 after the liquid formulations prepared at varying pHs shown in Table 1 were subjected to an acceleration test at 40° C. for 2 weeks. The results are shown in FIG. 2.

At a pH within the range of about 5 to 7, the production ratio of desialylated G-CSF was very low. Example 3: Effect of the concentration of surfactants on the adsorption of G-CSF to containers.

To a mixture of 250 mg of G-CSF and 5.844 g of sodium chloride was added Polysorbate 20 to the concentrations shown in the following Table 2 and the mixture was adjusted at pH 6.5 with a sodium phosphate buffer and brought to a total amount of 1 L.

TABLE 2

| Poly-sorbate 20 | G-CSF | Sodium chloride | Sodium phosphate buffer | pH | Total amount |
|---|---|---|---|---|---|
| 0 g | 250 mg | 5.844 g | Equivalent to 15 mM | 6.5 | 1 L |
| 0.02 g | 250 mg | 5.844 g | Equivalent to 15 mM | 6.5 | 1 L |
| 0.05 g | 250 mg | 5.844 g | Equivalent to 15 mM | 6.5 | 1 L |
| 0.1 g | 250 mg | 5.844 g | Equivalent to 15 mM | 6.5 | 1 L |
| 0.2 g | 250 mg | 5.844 g | Equivalent to 15 mM | 6.5 | 1 L |
| 0.5 g | 250 mg | 5.844 g | Equivalent to 15 mM | 6.5 | 1 L |

Each G-CSF formulated solution shown in Table 2 was sterilely prepared and filtrated, after which 1 mL each was sterilely packed into a vial (untreated white glass vial (5 mL) made by Murase Glass) and the G-CSF content was determined by reverse phase high-performance liquid chromatography described in Method 1 immediately after packing and after the lapse of 24 hours after packing.

The G-CSF content determined by this method was used to calculate the adsorption inhibition rate (%) after the lapse of 24 hours after packing according to the following equation.

Adsorption inhibition rate (%)=[(G-CSF content after the lapse of 24 hr after packing)/(G-CSF content immediately after packing)]×100

Figure 3:
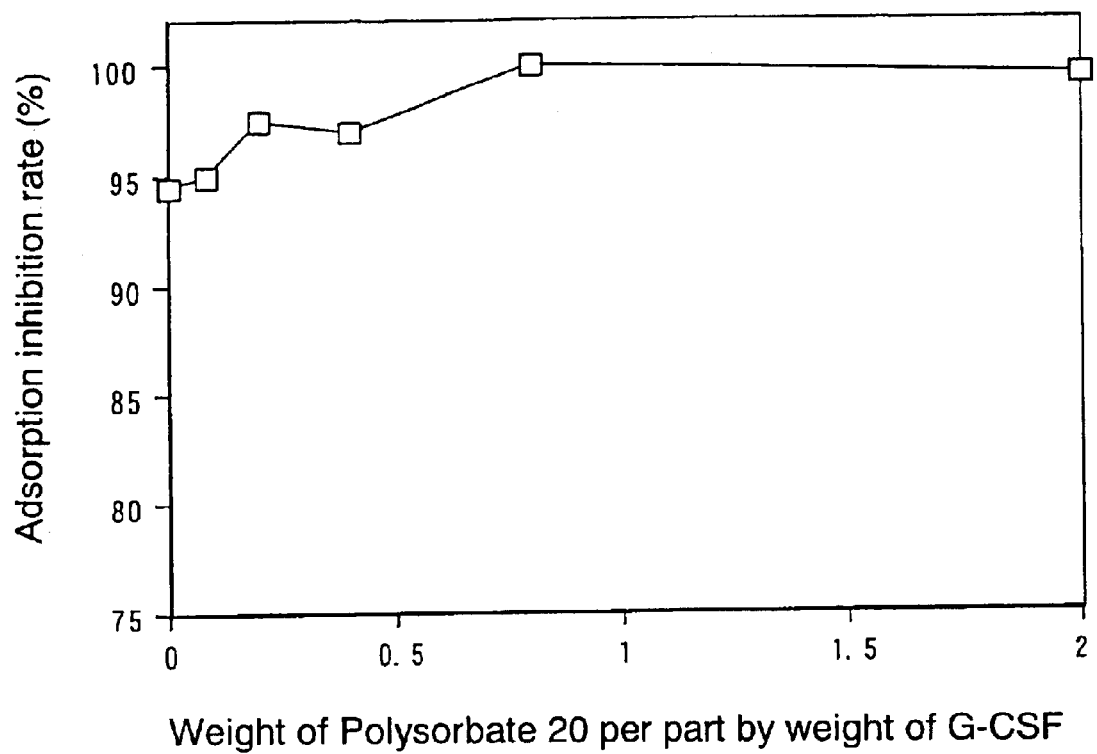
FIG. 3 is a graph showing the relationship between the part by weight of Polysorbate 20 per part by weight of G-CSF and the adsorption inhibition rate after the lapse of 24 hours after packing.

The results are shown in Table 3 and FIG. 3.

TABLE 3

| Parts by weight* | Adsorption inhibition rate |
|---|---|
| 0 | 94.5% |
| 0.08 | 95.0% |
| 0.2 | 97.5% |
| 0.4 | 97.0% |

TABLE 3-continued

| Parts by weight* | Adsorption inhibition rate |
|---|---|
| 0.8 | 100% |
| 2 | 99.5% |

*Parts by weight: Parts by weight of Polysorbate 20 per part by weight of G-CSF

Adsorption inhibition rates were sufficient even when the Polysorbate concentration was 1 part by weight or less per part by weight of G-CSF.

Example 4

Stability of Formulations Packed in a Vial or Syringe

A formulated solution containing 250 mg of G-CSF, 0.1 g of Polysorbate 20 and 7 g of sodium chloride in a total amount of 1 L and adjusted to pH 6.5 with a sodium phosphate buffer was sterilely prepared and filtrated, after which 1 mL each was sterilely packed into a vial (see above) or syringe (Hypac SFC, 1 mL long, made by Nippon Becton Dickinson & Co,. Ltd.) and sealed to prepare a G-CSF liquid formulation shown in Table 4.

TABLE 4

| G-CSF | Poly-sorbate 20 | Sodium chloride | Sodium phosphate buffer | pH | Total amount |
|---|---|---|---|---|---|
| 250 mg | 0.1 g | 7.0 g | 15 mM | 6.5 | 1 L |

The thus sterilely prepared formulation containing 250 μg/mL of G-CSF was allowed to stand in an incubator at 40° C. for 2 weeks or in an incubator at 25° C. for 6 months.

The content of G-CSF in each vial or syringe was determined according to Method 1, and the percentage of remaining G-CSF after acceleration at 40° C. for 2 weeks and the percentage of remaining G-CSF after storage at 25° C. for 6 months were calculated according to the equation of Method 1.

The results are shown in Table 5.

TABLE 5

| | Remaining percentage | |
|---|---|---|
| Container type | Acceleration at 40° C., 2 weeks | Storage at 25° C., 6 months |
| Vial | 89.6% | 98.4% |
| Syringe | 90.7% | 97.9% |

G-CSF formulations of the present invention showed excellent stability, as demonstrated by the remaining percentage of 75% or more after acceleration at 40° C. for 2 weeks and the remaining percentage of 95% or more after storage at 25° C. for 6 months in both vial and syringe.

INDUSTRIAL APPLICABILITY

G-CSF-containing formulations of the present invention, which contain a very small amount of surfactants such as 1 part by weight or less per part by weight of G-CSF, can effectively solve the problems related to loss of active ingredients or decrease of activity due to aggregation, polymerization, oxidation or adsorption to container walls caused by extrinsic factors such as the temperature of G-CSF present in a small amount in the formulations, humidity, oxygen, UV rays, etc. Therefore, the present invention provides a liquid formulation which reduces complexity and costs in the production process and which is stable during even extended storage.

What is claimed is:

1. A stable granulocyte colony-stimulating factor-containing formulation comprising a granulocyte colony stimulating factor having a sugar chain and at least one pharmaceutically acceptable non-ionic surfactant in an amount of 1 part by weight or less per part by weight of the granulocyte colony-stimulating factor and having a pH of 6–6.8, said formulation being substantially free from protein as a stabilizer.

2. The granulocyte colony-stimulating factor-containing formulation of claim 1 wherein the surfactant is contained in an amount ranging from 0.2 to 1 parts by weight per part by weight of the granulocyte colony-stimulating factor.

3. The granulocyte colony-stimulating factor-containing formulation of claim 2 wherein the surfactant is contained in an amount ranging from 0.2 to 0.8 parts by weight per part by weight of the granulocyte colony-stimulating factor.

4. The granulocyte colony-stimulating factor-containing formulation of claim 2 wherein the surfactant is contained in an amount ranging from 0.4 to 0.8 parts by weight per part by weight of the granulocyte colony-stimulating factor.

5. The granulocyte colony-stimulating factor-containing formulation of claim 2 wherein the surfactant is contained in an amount of 0.4 or 0.8 parts by weight per part by weight of the granulocyte colony-stimulating factor.

6. The granulocyte colony-stimulating factor-containing formulation of claim 1 wherein the surfactant is at least one non-ionic surfactant selected from the group consisting of sorbitan fatty acid esters, glycerin fatty acid esters, polyglycerin fatty acid esters, polyoxyethylene sorbitan fatty acid esters, polyoxyethylene sorbitol fatty acid esters, polyoxyethylene glycerin fatty acid esters, polyethylene glycol fatty acid esters, polyoxyethylene alkyl ethers, polyoxyethylene polyoxypropylene alkyl ethers, polyoxyethylene alkyl phenyl ethers, polyoxyethylene hardened castor oils, polyoxyethylene beeswax derivatives, polyoxyethylene lanolin derivatives, and polyoxyethylene fatty acid amides.

7. The granulocyte colony-stimulating factor-containing formulation of claim 1 wherein the surfactant is a polyoxyethylene sorbitan fatty acid ester selected from the group consisting of Polysorbate 20 and Polysorbate 80.

8. The granulocyte colony-stimulating factor-containing formulation of claim 1, which has a pH of 6.2–6.8.

9. The granulocyte colony-stimulating factor-containing formulation of claim 1, which is packed in a vial, ampoule or prefilled syringe.

* * * * *